US006419957B1

(12) United States Patent
Lenaerts et al.

(10) Patent No.: US 6,419,957 B1
(45) Date of Patent: Jul. 16, 2002

(54) CROSS-LINKED HIGH AMYLOSE STARCH HAVING FUNCTIONAL GROUPS AS A MATRIX FOR THE SLOW RELEASE OF PHARMACEUTICAL AGENTS

(75) Inventors: Vincent Lenaerts, Westmount; Francois Chouinard, Laval; Mircea Alexandru Mateescu; Pompilia Ispas-Szabo, both of Montreal, all of (CA)

(73) Assignee: Labopharm, Inc., Laval (CA)

( * ) Notice: Subject to any disclaimer, the term of this patent is extended or adjusted under 35 U.S.C. 154(b) by 0 days.

(21) Appl. No.: 09/257,090

(22) Filed: Feb. 24, 1999

Related U.S. Application Data

(63) Continuation-in-part of application No. 09/028,385, filed on Feb. 24, 1998, now Pat. No. 6,284,273.
(51) Int. Cl.[7] .............................. A61K 9/14; A61K 9/20; A61K 9/16
(52) U.S. Cl. .................. 424/488; 424/489; 424/464; 424/465; 424/497; 424/486
(58) Field of Search ................................ 424/488, 489, 424/464, 465, 497, 486; 514/160

(56) References Cited

U.S. PATENT DOCUMENTS 5,830,884 A * 11/1998 Kasica et al.

OTHER PUBLICATIONS

Lenaerts et al., Controlled release of theophylline from cross–linked amylose tablets, 15 (1991), pp. 39–46.*

Mateescu et al., "A new amyloclastic method for the selective detemrination of alpha–amylase using cross–linked amylose as an insoluble substrate", 124 (1983), pp. 319–323.*

* cited by examiner

Primary Examiner—Thurman K. Page
Assistant Examiner—Amy E Pulliam
(74) Attorney, Agent, or Firm—Pennie & Edmonds LLP

(57) ABSTRACT

The present invention relates to a solid slow release oral pharmaceutical dosage unit resistant to amylase which comprises a solid dosage unit made up of an admixture of a therapeutic dosage of an orally effective pharmaceutical agent, an optional polysaccharide or polyol, and high amylose starch, wherein the cross-linking of the high amylose starch has been carried out with a cross-linking agent with from about 0.1 g to about 40 g of cross-linking agent per 100 g of high amylose starch. In a preferred embodiment of the invention, the high amylose starch is modified with a functional group-attaching reagent that covalently bonds functional groups thereto.

6 Claims, 8 Drawing Sheets

CROSS-LINKED HIGH AMYLOSE STARCH HAVING FUNCTIONAL GROUPS AS A MATRIX FOR THE SLOW RELEASE OF PHARMACEUTICAL AGENTS

This is a continuation-in-part of application Ser. No. 09/028,385, filed Feb. 24, 1998, now U.S. Pat. No. 6,284,273, which is incorporated herein in its entirety.

FIELD OF THE INVENTION

The present invention relates to cross-linked high amylose starch and in particular, cross-linked high amylose starch having functional groups. Such cross-linked high amylose starch imparts sustained release to a pharmaceutical agent when compressed in a tablet form.

BACKGROUND OF THE INVENTION

The controlled release of bioactive molecules, e.g., pharmaceutical agents, has been the subject of extensive research over the last half of the twentieth century. The controlled release of pharmaceutical agents is of high importance for biopharmaceutical applications. Long acting doses of a variety of drugs are now available, allowing once or twice-a-day dosage regimens where immediate release forms called for multiple and sometimes impractical administrations. Effective slow-release dosage regimens have demonstrated superior patient compliance and hence improved efficacy over multiple immediate release forms.

There are several types of polymers that have been used as a matrix for the slow-release of drugs. Thus, polymeric materials such as polyvinyl chloride, polyethylene polyamides, ethylcellulose, silicone, poly (hydroxyethyl methacrylate), other acrylic co-polymers, polyvinylacetate-polyvinyl chloride copolymers and other polymers have been described as an adequate matrix for tablet preparation (see for example U.S. Pat. Nos. 3,087,860; 2,987,445; and *Pharm. Acta Helv.*, (1980), 55:174–182, Salomon et al.).

Polysaccharides have been used widely in pharmaceutical, chemical, and biochemical drug delivery. This family of natural polymers has been applied to the are of controlled release coatings, matrices, macromolecular carriers and biodegradable carriers. One of the most frequent problems associated with the use of polysaccharides, such as starch, as drug delivery agents is its susceptibility to degradation by intestinal polysaccharidases such as α-amylase. The use of polysaccharides in colonic drug delivery has been reviewed (Critical Reviews™ in Therapeutic Drug Carrier Systems, 13 (3 & 4):185–223 (1996).

Starch is, however, one of the most attractive biopolymers for use as a drug delivery agent since it can be mass produced with a high purity at a very economical price. Recently, in order to apply amylose to the controlled release field, a chemically modified amylose was prepared by cross-linking amylose in the gelatinized state as described in U.S. Pat. No. 5,456,921.

Amylose is a natural substance obtained from starch. It is essentially a linear, non-branched, polymer of glucopyranose units with α-D-(1–4) linkages. In starch, amylose is usually accompanied by amylopectin, which is a branched polyglucose polymer with a significant frequency of branching points based on α-(1–6)-glucosidic bonds.

Cross-linked amylose (CLAm) is an excipient for the controlled release of drugs in solid drug dosage forms. CLAm is produced by the reaction of amylose with a suitable cross-linking agent in an alkaline medium. Different degrees of cross-linking (CLAx) can be obtained by varying the ratio of cross-linking agent, such as epichlorohydrin, to amylose in the reaction vessel where x indicates the amount (g) of cross-linking agent used for cross-linking 100 g of amylose (i.e., CLAx with x=0, 6, 11, 15 or 30).

CLAm tablets are prepared by direct compression, and are highly resistant to mechanical stress in the dry state. When placed in contact with aqueous fluids, water diffuses into the CLAm matrix, with subsequent formation of a gel layer. Progressive water sorption leads to significant swelling of the matrix. With degrees of cross-linking below 11, the swollen polymeric matrix does not undergo any erosion during in vitro experiments performed in the absence of amylase. Amylase found in the human duodenum catalyzes the hydrolysis of amylose, drastically reducing its sustained-release properties.

Accordingly, it would be desirable to provide a slow-release system having greater resistance to amylase-induced degradation, with overall improved sustained release properties.

Another feature of cross-linked amylose is its ability to release drugs at a constant rate, following zero-order kinetics, such as described in S.T.P. *Pharma* (1986), 2:38–46 (Peppas et al.). The approach called "swelling-controlled" systems consists of glassy polymers into which a water front penetrates at a constant rate. Behind this front, the polymer is in a rubbery state. Provided the drug diffusion coefficient in the rubbery polymer is much higher than in the glassy polymer, a zero order release can be achieved to a certain degree. However, the delivery rate is constant only for a limited fraction of the release, usually around 60% of the total amount of contained drug, and requires a low initial drug concentration.

X-ray diffraction studies show different morphologic forms for amylose in correlation with its origin, preparation mode or hydration state (French D. - "Organization of starch granules"—in Starch: Chemistry and Technology [Whistler R., L., BeMiller J., N. and Paschall E. F., Eds.], Acad. Press, 1984). The structures of A and B-type amylose are based on double helices parallel stranded and antiparallel packed, the individual strands being in a right-handed sixfold helical conformation (Wu H. C. and Sarko A., *Carbohydr. Res.*, 61:7–25, 1978). Amylose A contains 8 molecules of $H_2O$ and Amylose B (hydrated) contains 36 molecules of $H_2O$ per elementary cell unit. V-Amylose is made from single helix chains and exists as complexes with small organic molecules, water or iodine. Even though the inside of the helix channel of V-amyloses is primarily hydrophobic, intra-helical water has been found in anhydrous (Va), as well as in the hydrated (Vh) forms. Some intermolecular hydrogen bonds are formed through interstitial water molecules. It has been suggested that the presence of a substantial amount of complexing agent (e.g., ethanol) can mainly stabilize single helices of amylose, whereas a predominance of water can induce conformational changes leading to the formation of double helices (Buleon A., Duprat F., Booy F. P. and Chanzy H., Carbohydr. *Polymer,* 4:61–173, 1984). All forms of amylose become B-type in gel phase (Wu H. C. and Sarko A., *Carbohydr. Res.,* 61:27–40, 1978); the interchange of morphological structures tends to reach the more stable double helix form with the corresponding molecules of water.

Accordingly, it would be desirable to provide a slow release system following a zero-order kinetics, and allowing a controlled release of a drug at a constant rate until all the drug is released, whatever the concentration of the drug in the system.

Citation or identification of any reference in Section 2 of this application shall not be construed as an admission that such reference is available as prior art to the present invention.

SUMMARY OF THE INVENTION

In accordance with the present invention there is now provided a solid slow release oral pharmaceutical dosage unit which comprises a solid dosage unit made up of an admixture of a therapeutic dosage of an orally effective pharmaceutical agent and covalent cross-linked polymer of high amylose starch made by reacting high amylose starch with a suitable cross-linking agent, wherein the covalent cross-linking of the polymer has been carried out with from about 0.1 to about 40 g of cross-linking agent per 100 g of amylose.

In a preferred embodiment of the invention, the cross-linked polymer is modified with a functional group.

In a further aspect of the invention, there is provided a solid slow release oral pharmaceutical dosage unit made up of an admixture of a therapeutic dosage of an orally effective pharmaceutical agent, an optional polysaccharide or polyol and a cross-linked polymer of high amylose starch made by reacting high amylose starch with a suitable cross-linking agent.

In another aspect of the invention, the pharmaceutical agent is present in the tablet in an amount of from 0.01 to 80% w/w.

In a further aspect of the invention, a method is described to obtain a matrix resistant to all types of amylase, obviating the concern over premature degradation of the tablet and accelerated release of the orally effective pharmaceutical agent.

In a still further aspect of the invention, the invention provides cross-linked amylose having functional groups, prepared by a process comprising the steps of:

(a) reacting high amylose starch with a cross-linking agent at a concentration of about 0.1 g to about 40 g of cross-linking agent per 100 g of high amylose starch to afford cross-linked amylose; and (b) reacting the cross-linked amylose with a functional group-attaching reagent at a concentration of about 75 g to about 250 g of functional group-attaching reagent per 100 g of cross-linked amylose to afford the cross-linked amylose having functional groups.

In a still further aspect, the invention provides a solid controlled-release oral pharmaceutical dosage unit in the form of a tablet comprising a blend of about 0.01% to about 80% by weight of a pharmaceutical agent and about 20% to about 99.99% by weight of the cross-linked amylose having functional groups.

In a still further aspect, the invention provides a method for imparting sustained release to a pharmaceutical agent, comprising the steps of:

(a) providing the pharmaceutical agent in dry powder form;

(b) blending the pharmaceutical agent with the cross-linked amylose having functional groups; and (c) compressing the blend to form a tablet.

The present invention may be understood more fully by reference to the following figures, detailed description and illustrative examples which are intended to exemplify non-limiting embodiments of the invention.

DETAILED DESCRIPTION OF THE INVENTION

Figure 1:
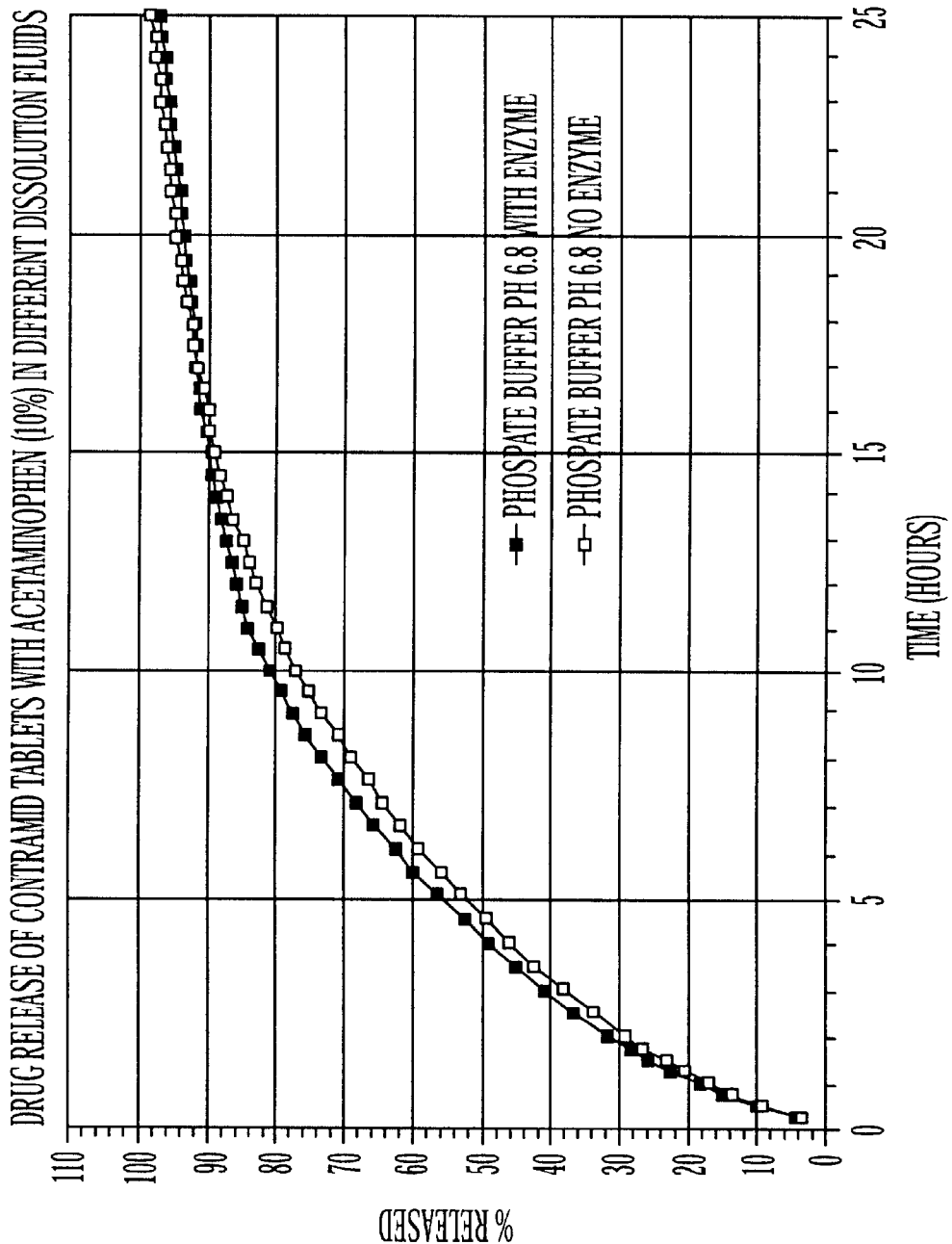
FIGS. 1 and 2 illustrate the release characteristics of cross-linked high amylose starch tablets containing acetaminophen and pseudoephedrine, respectively. The data indicate that the tablets are not sensitive to enzymatic degradation by amylase. The specific type of amylose used in these examples contained at least 20% amylopectin and was cross-linked with sodium trimetaphosphate.
Figure 2:
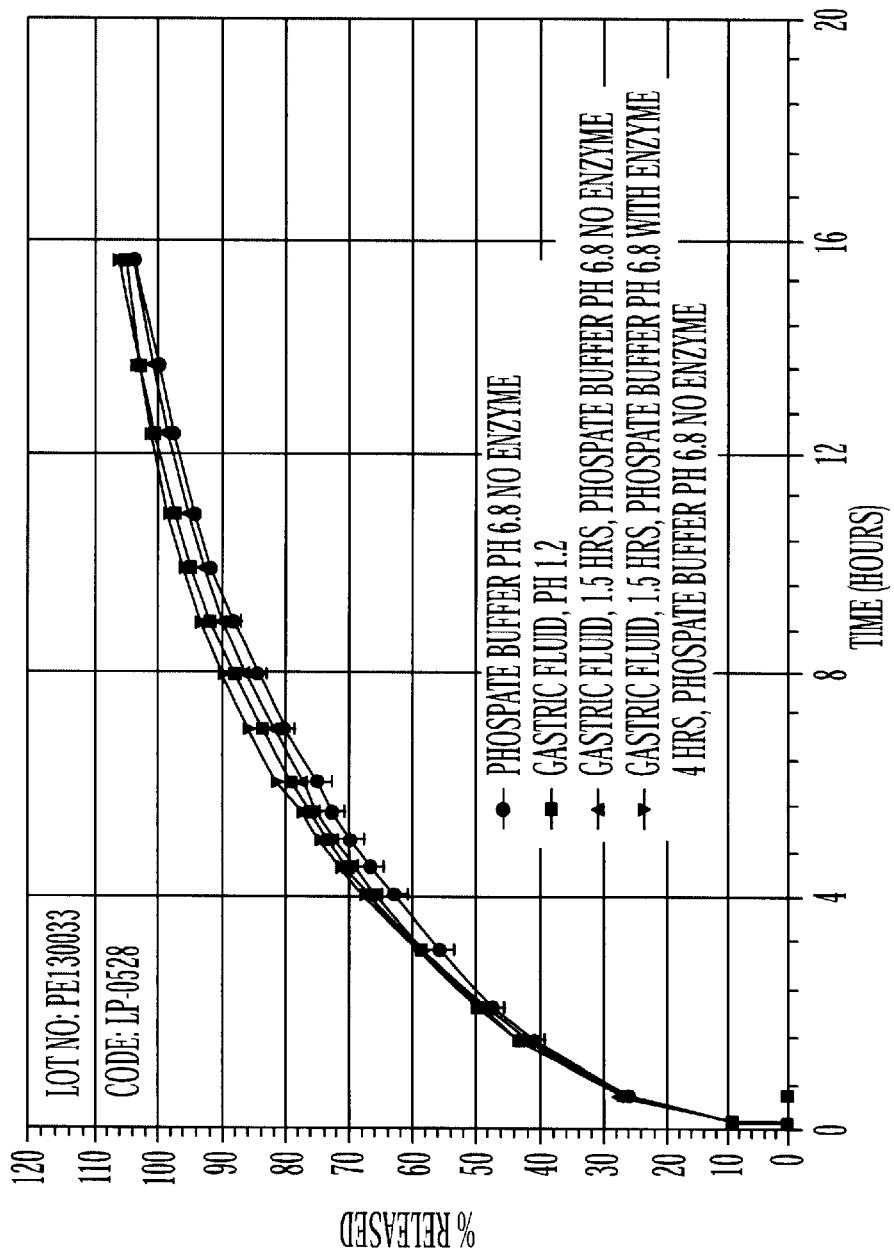

Cross-linking of amylose can be carried out in the manner described in BIOCHEMIE 1978, 60, 535–537 (Mateescu) by reacting amylose with epichlorohydrin in an alkaline medium. In the same manner, amylose can also be cross-linked with other cross-linking agents including, but not limited to, 2,3-dibromopropanol, epichlorohydrin, sodium trimetaphosphate, linear mixed anhydrides of acetic and di- or tribasic carboxylic acids, vinyl sulfone, diepoxides, cyanuric chloride, hexahydro-1,3,5-trisacryloyl-s-triazine, hexamethylene diisocyanate, toluene 2,4-diisocyanate, N,N-methylenebisacrylamide, N,N'-bis (hydroxymethyl) ethyleneurea, phosgene, tripolyphosphate, mixed carbonic-carboxylic acid anhydrides, imidazolides of carbonic and polybasic carboxylic acids, imidazolium salts of polybasic carboxylic acids, guanidine derivatives of polycarboxylic acids, and esters of propanoic acid.

It has been found that high amylose starch can be admixed with additives prior to reaction with the cross-linking agents. The resulting product is useful as a matrix for sustained release of pharmaceutical agents.

Suitable agents that could be used as additives to high amylose starch for sustained release prior to cross-linking of the high amylose starch include, but are not limited to, polyvinyl alcohol, β-(1–3) xylan, xanthan gum, locust bean gum and guar gum.

Essentially, the high amylose starch is swollen in water by generally known gelatinization techniques such as alkaline or heat treatment and, after homogenization, an appropriate amount of cross-linking agent is added. After substantial homogenization, the reaction medium is transferred onto a water bath and heated for one hour at a temperature of from 40° to 45° C. and the temperature is then raised from 60° to 75° C. for a further period of from 1 to 2 hours after which time the reaction is complete. The duration of heating can be varied as well as the amount of cross-linking agent used in the reaction.

The resulting cross-linked material is then sieved, and the granules ranging from about 25 to about 700 um are collected for the preparation of the slow-release tablet of the present invention. The granules of 25 to about 300 um representing at least 50% of the granules are selected for use in accordance with the presented invention.

The preferred cross-linked polymers of high amylose starch with cross-linking agents suitable for the purposes of the present invention are those where from about 0.1 to about 40 g of cross-linking agent have been used to cross-link 100 g of high amylose starch.

It has been surprisingly found that when a mixture of amylose and amylopectin between about 10–60% amylopectin by weight is cross-linked by a cross-linking agent comprising sodium trimetaphosphate, 2,3-dibromopropanol, epichlorohydrin, and epibromohydrin or mixed with a suitable polysaccharide or polyol and compressed into tablets, those tablets are resistant to amylase degradation provided that the lubricant used for tableting is not magnesium stearate. These tablets can then be used for the controlled release of oral pharmaceutical agents. Conversely, when the objects of the invention are dispersed as a powder in an amylase medium, they are readily degraded. Therefore, when placed in a tablet, it was entirely unexpected that the objects of the invention were stable to amylase.

It has also been surprisingly found that when covalently cross-linked high amylose starch of the invention is exposed to water, it predominantly forms a double helix similar to the B-form of amylose. Upon placement of a high amylose cross-linked starch tablet in water, a gel is formed very quickly at the polymer surface. As the progression of the gel front toward the center of the tablet ceases rapidly, water diffuses into the polymer. As water continues to penetrate, the water gradient in the core progressively diminishes and the core expands. This process goes on for several hours, until the core turns into a gel and equilibrium swelling is reached. In the gel state, the cross-linked high amylose starch, which was initially arranged mainly in the amorphous state and in V type single helices, progressively adopts the B-type double helices conformation, forming a three-dimensional physical network. Both amylose and PVA can adopt helical conformations. PVA is an interesting polymer with alternating hydrophilic (CHOH) and hydrophobic ($CH_2$) groups, and consequently, undergoes lower swelling in water than amylose. In one feature of the invention, PVA can be mixed with high amylose starch. The mixture is then cross-linked and compressed into tablets exhibiting sustained release properties and resistance to degradation by alpha-amylase.

It has further been surprisingly found that when cross-linked high amylose starch is modified with functional groups, e.g., carboxymethyl (—$CH_2COOH$) or aminoethyl (—$CH_2CH_2NH_2$) groups, such modified cross-linked high amylose starch, when compressed into tablets, is exceedingly resistant to amylase-catalyzed degradation that occurs in the human duodenum. This result is highly desirable in that the slower the rate of dissolution, the greater the degree of sustained release of pharmaceutical agent from the tablet. This leads to an enhanced drug benefit over a given unit of time, and allows for the administration of lower and/or fewer doses of the drug over a given unit of time. Accordingly, such tablets comprising cross-linked high amylose starch that is modified with groups having functional groups are highly useful for the sustained release of oral pharmaceutical agents.

It has been found that cross-linked high amylose starch can be modified with functional groups by reacting the cross-linked high amylose starch with a functional group-attaching reagent. Without being bound by any particular theory, the functional group-attaching reagent reacts with hydroxyl groups of the starch molecule forming covalent bonds therewith. Generally, the functional group-attaching reagent has the formula Y—A—COOH, Y—A—$NH_2$, Y—A—$NR_3^+X^-$, Y—A—SH, Y—A—$SO_3H$ and Y—A—OH, wherein A is a moiety capable of forming a covalent bond with a starch hydroxyl group, Y is a leaving group that departs upon A's formation of a covalent bond with a starch hydroxyl group, and R is alkyl or hydrogen. Suitable A groups include, but are not limited to -alkyl-, —C(O)alkyl-, —C(O)N(H)alkyl-, —C(O)Oalkyl- and the like. In the case of Y—A—OH, A is an aromatic group. Preferably, the functional group-attaching reagent is monochloroacetic acid or 2-chloroethylamine hydrochloride.

Generally, the reaction between the cross-linked high amylose starch and the functional group-attaching reagent is carried out at a concentration of about 75 g to about 250 g of functional group-attaching reagent per 100 g of cross-linked high amylose starch, in the presence of aqueous base, e.g., 2–12N NaOH. The reaction is preferably performed at elevated temperature, e.g., at about 50° C. to about 100° C.

When the functional group-attaching reagent is monochloroacetic acid, preferably a concentration of about 75 g to about 250 g of monochloroacetic acid per 100 g of cross-linked high amylose starch is used. When the functional group-attaching reagent is 2-chloroethylamine hydrochloride, preferably a concentration of about 100 g to about 150 g of 2-chloroethylamine hydrochloride per 100 g of cross-linked high amylose starch is used. Typically, the functional group-attaching reagent will attach about 0.4 to about 1 mequiv. of functional group/g of cross-linked high amylose starch.

Applicants have found that the modified cross-linked high amylose starch of the present invention is useful as a carrier polymer for pharmaceutical agents that are administered orally, in view of its high resistance to amylase degradation and enhanced dissolution properties. Such modified cross-linked high amylose starch confers desirable slow-release properties to orally administered tablets containing pharmaceutical agents.

Accordingly, the invention provides a solid controlled-release oral pharmaceutical dosage unit. Such dosage unit is preferably in the form of a tablet, although capsules, lozenges and troches are also contemplated. The solid controlled-release oral pharmaceutical dosage unit of the present invention comprises a blend of about 0.01% to about 80% by weight of a pharmaceutical agent, and of about 20% to about 99.99% by weight of the modified cross-linked high amylose starch described above. Preferably the dosage unit comprises about 5% to about 20% by weight of a pharmaceutical agent. The pharmaceutical agent is preferably in the form of a dry powder.

Such pharmaceutical agent is any drug that can be orally administered. Preferably, the pharmaceutical agent is pseudoephedrine hydrochloride, acetaminophen or diclofenac sodium, verapamil, glipizide, nifedipine, felodipine, batahistine, (R)-albuterol, acrivastine, omeprazole, misoprostol, tramadol, oxybutinin, and salts thereof. In addition, the pharmaceutical agent can be an antifungal agent, such as ketoconazole, or an analgesic agent such as acetylsalicylic acid, acetaminophen, paracetamol, ibuprofen, ketoprofen, indomethacin, diflunisol, naproxen, ketorolac, diclofenac, tolmetin, sulindac, phenacetin, piroxicam, mefamanic acid, dextromethorphan, other nonsteroidal anti-inflammatory drugs including salicylates, pharmaceutically acceptable salts thereof or mixtures thereof.

Once the pharmaceutical agent and modified cross-linked high amylose starch are blended, generally by conventional means, the resulting blend is compressed to form a tablet. Preferably, the pressure used to compress the blend is equal to or exceeds 0.16 T/cm$^2$.

The present invention will be more readily understood by referring to the following examples which are given to illustrate the invention rather than limit its scope.

EXAMPLES

Experimental

Materials and Methods

Materials

High Amylose Starch: Hylon VII powder purchased from National Starch (A);

PVA powders (Aldrich) with different molecular masses (9000–146000 Da), and 80–89% hydrolysis degree (Hydrolysis degree is the number of acetate groups left after hydrolysis of polyvinyl-acetate (PVAc) to generate PVA, calculated in percentage from the initial number of acetate functional groups);

Epichlorohydrin, sodium trimetaphosphate (Sigma Chem Co.),

α-amylase (EC 3.2.1.1) from Bacillus species from Sigma Chemical Co., acetic acid glacial, monobasic and dibasic sodium phosphate (from Anachemia);

NaOH and acetone (ACS quality);

Synthesis of Cross-Linked Polymers-cross-linked High Amylose Starch (CLA), and Co-cross-linked High Amylose Starch-PVA

Synthesis of Cross-linked High Amylose Starch (CLA-0, CLA-3, CLA-6, CLA-8 and CLA-14)

For each synthesis, a quantity of 300 g of high amylose starch powder and a volume of 1.75 L of 0.85 N sodium hydroxide (55° C.) were mixed in a HOBART® planetary mixer tank N-50, maintaining the temperature at 50° C. for gelatinization. After 20 minutes of homogenization, a volume of 0 mL, 7.60 mL, 15.24 mL, 20.30 mL or 38.10 mL of epichlorohydrin (corresponding to the required cross-linking degree) was respectively added in each synthesis batch. For instance, for CLA-6 a volume of 15.24 mL of epichlorohydrin corresponding to 18 g (d=1.19 g/mL) was added. Each reaction mixture was again homogenized for 20 minutes. The reaction was continued for a period up to 1 h, under moderate heating (40–70° C). The mixture was neutralized with acetic acid, and then thoroughly washed on a Büchner funnel with a solution of water/acetone (15:85 v/v) in a first step and then with water/acetone (60:40). The CLA was finally dried with acetone and then exposed to the air during 24 hours. Other drying procedures (spray-drying, lyophilization) can also be used. The dry polymer was sieved (mesh openings of 75–300 um) and stored at room temperature.

Other CLA polymers with different cross-linking degrees (x) can be obtained in similar conditions, with the mention that the added quantities should be of "x" g cross-linking reagent/100 g of amylose.

Synthesis of Co- CL(A-PVA) Polymer Co- CL(A-PVA)-6 Polymer Synthesis, with Different Ratios A/PVA (3/1; 1/1: 1/3)

The cross-linking degree was maintained constant (clx=6) and different amylose/PVA initial polymer ratios were prepared: A/PVA—(3/1) corresponding to 225 g A/75 g PVA; A/PVA=(1/1) corresponding to 150 g A/150 g PVA; A/PVA—(1/3) corresponding to 75 g A/225 g PVA.

For each synthesis, the required amount of PVA powder (MW 9,000–146,000, 87–89% hydrolysis degree) was suspended in 1 L of 1.5 N sodium hydroxide and heated at 95° C. with strong stirring. After the system became macroscopically homogeneous, the temperature was decreased at 50° C. Separately, for each synthesis, the corresponding amount of high amylose starch (Hylon VII) was suspended in 750 mL cold distilled water in the HOBART® mixer and heated, under stirring, at 50° C. Subsequently, the PVA/NaOH solution was slowly added to the corresponding high amylose starch suspension, under continuous stirring and the system kept for 20 min at controlled temperature (50–55° C.) for high amylose starch gelatinization.

Synthesis of CL(A-PVA)-6 with Epichlorohydrin as Cross-linking Agent

For each gelatinized batch (at 40–60° C.), amount of 18 g epichlorohydrin (clx=6) was added. After 1 hour at 50° C., the mixture was neutralized with 0.75 M acetic acid solution, and then washed and dried with acetone. Other drying procedures (spray-drying, lyophilization) can also be used. The powders were sieved and kept in dark bottles at room temperature.

Synthesis of CL(A-PVA)-6 with Sodium-trimetaphosphate (STMP) as Cross-linking Agent The gelatinized batch, was treated with an amount of 18 g STMP. After 1 h at 50° C., the mixture was neutralized with 0.75 M acetic acid solution, and then washed and dried with acetone. Other drying procedures (spray-drying, lyophilization) can also be used. The powders were sieved and kept in dark bottles at room temperature.

Synthesis of CLA-20 with Epichlorohydrin as Cross-linking Agent 150 g of amylose was suspended in 750 mL of cold distilled water, in a reactor. The suspension was warmed to 50° C. under stirring, and a volume of 1 L of 1.5 N NaOH (60 g/L) was slowly added (over about 8 min) to the amylose suspension. The medium was maintained for another 20 min at 50° C. with stirring for gelatinization. Then an amount of 25.4 mL of epichlorohydrin (d=1.19 g/mL) was added slowly (over 5 min), at a constant rate. The reaction medium was maintained with stirring, at 50° C. for 1 h to effect cross-linking.

Neutralization was accomplished by adding 2.5 L of distilled water to the reaction medium. Then, a solution of acetic acid (88 mL of glacial acetic acid in 600 mL distilled water, completed with another volume of 1050 mL distilled water pre-heated at 50° C.) was slowly introduced to the CLA-20 suspension with stirring, up to a final pH of 6.8–7.0. The suspension was then slowly cooled to 20° C.

A solution of acetone-water (85/15 v/v) was prepared, and 1 L of this solution was added slowly, under stirring, to a 1 L suspension of CLA-20. This medium was left, under stirring, at 4° C., for 20 min, and filtered. The gel remaining on the filter was resuspended in 1 L of acetone/water solution (60/40 v/v), maintained for 20 min under stirring at 4° C., and filtered. This washing with acetone/water (60/40) was repeated two more times.

The gel obtained from last filtration was recovered and resuspended in 400 mL of acetone. The medium was maintained for 20 min under stirring at 4° C., and filtered. This operation was repeated two more times (but without keeping the suspension for 20 min under stirring at 4° C.), and filtered. The resulting powder was dried by evaporation of acetone and then sieved, retaining fractions of 300–500 μm for the subsequent steps.

Synthesis of Carboxymethyl Amylose (CM-CLA-20)

10 g of CLA-20 was suspended in 400 mL distilled water, for swelling. The suspension was filtered, and the gel recovered and resuspended in 200 mL of 10 M NaOH. Then, 20 g of monochloroacetic acid (dissolved in 20–25 mL distilled water) was added to the basic suspension of CLA-20. The reaction medium was homogenized for 20 min on ice bath and then placed in a water bath at 75° C. for 1 h to effect carboxymethylation.

After the reaction was complete, the suspension was filtered, resuspended in distilled water and filtered again on Büchner funnel, measuring the pH in the filtrate. The gel was washed on the filter, until a pH 6.5–7.0 was reached. Then, the gel was resuspended in 1 L of distilled water, and a 1 L solution of acetone/water (85/15 v/v) was added to the suspension of CM-CLA-20 slowly and under stirring. The medium was kept, under stirring, at 4° C. for 20 min, and filtered. The gel remaining on the filter was resuspended in 0.5 L of acetone/water solution (60/40 v/v), maintained for 20 min under stirring at 4° C., and filtered. This washing with acetone/water (60/40) was repeated two more times.

The gel obtained from the last filtration was recovered, resuspended in 400 mL of acetone, maintained for 20 min under stirring at 4° C., and filtered. This operation was repeated two more times (but without keeping the suspension for 20 min under stirring at 4° C.) and filtered. The resulting CM-CLA-20 powder was finally dried by evaporation.

The degree of substitution of hydroxyl groups was evaluated by potentiometric titration of carboxymethyl groups (device: Corning-ion analyzers 250) with 0.1 N NaOH.

The substitution degree of the hydroxyl groups in CM-CLA-20 was evaluated on the basis of the ionic exchange capacity of the CM- derivative. The obtained capacity was of 0.4–1 mequiv/g—a value comparable to the capacities of other ionic exchangers, i.e., CM-Cellulose).

Hydrophilic Properties of CLA-20 and CM-CLA-20

Figure 3:
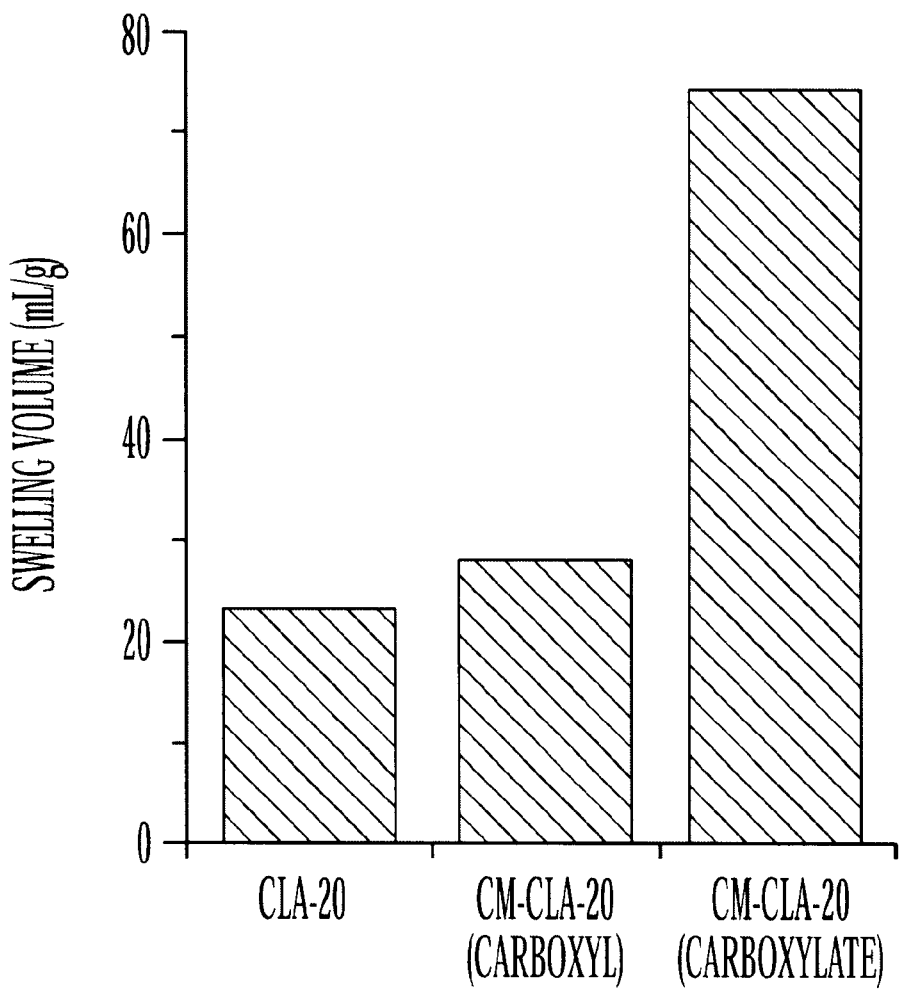
FIG. 3 is a bar graph showing swelling volume at equilibrium of CLA-20 and CM-CLA-20 (carboxyl and carboxylate sodium salt) measured in distilled water at 25° C.
Figure 4:
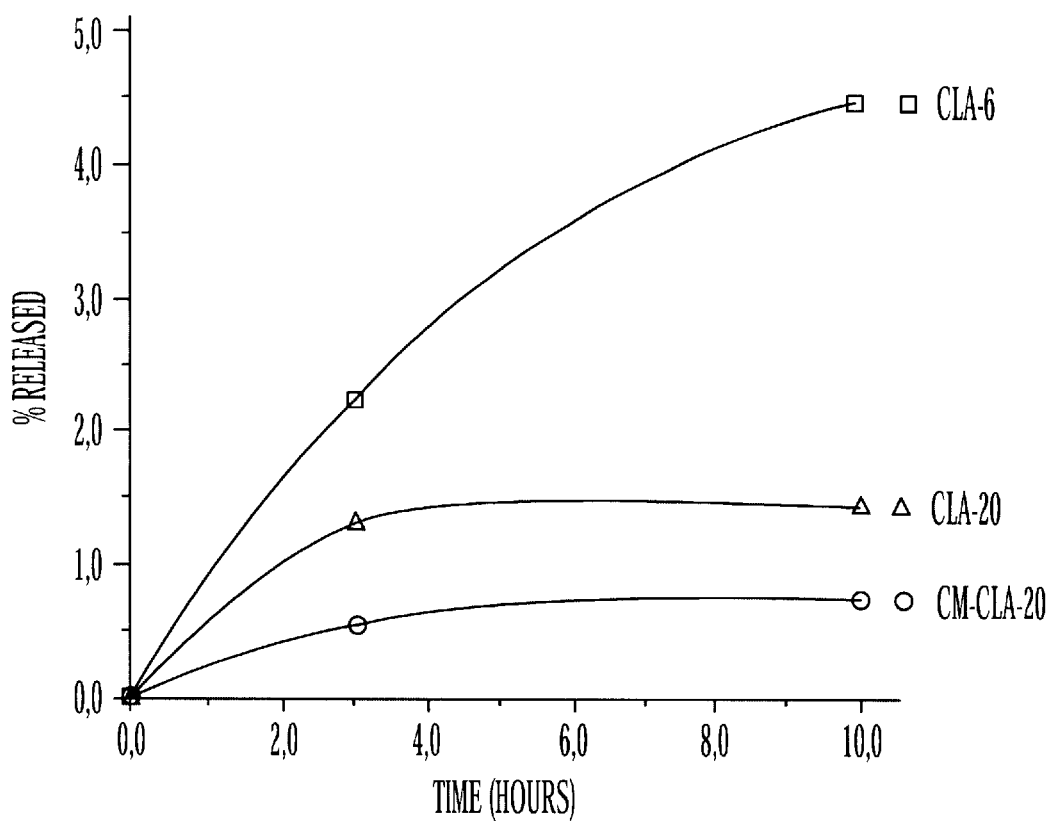
FIG. 4 is a line graph showing amylolysis of CLA-6, CLA-20 and CM-CLA-20.

One of the final steps in the CM-CLA-20 synthesis is the neutralization of the polymeric suspension. This can be performed using acid (i.e., acetic acid or HCl), leading to the CM-CLA having carboxyl groups in protonated form (—COOH), or by thoroughly washing with water, yielding the CM-CLA-20 having carboxylic functions as carboxylate salt forms (—COO$^-$Na$^+$). The carboxylate salt form is highly hydrophilic, generating an expanded network. Without being bound by any particular theory, Applicants believe that polymers that provide a high swelling volume have a lower viscosity in vivo, which permits enhanced diffusion of water and solutes from the polymer matrix to the duodenum. The differences in hydration between the salt and protonated forms of CM-CLA-20, are clearly presented in FIG. 3.

When filtered, the protonated form produced a consistent slurry with a moderate retention of water. Washing with 0.5 M NaCl resulted in a very small reduction of volume. When the salt formed, a voluminous gel material was filtered, a swelling approximately three times greater (FIG. 3) was obtained. Without being bound by any particular theory, more solvation water was retained (hydration of Na$^+$ cations of the carboxylate form) in addition to the water molecules retained into the network by available hydroxyl groups hydration. In this case, the washing with 0.5 M NaCl generated a decrease of about 50% of the swelling, but the final volume of this carboxylate form was still higher than the protonated form. By washing with 0.5 M NaCl, part of water trapped into the network was probably eliminated by osmosis.

Susceptibility to Amylolysis of CLA-6, CLA-20 and CM-CLA-20

Amylolysis was quantified from the amounts of maltose liberated by amylolysis of the three substrates (CLA-6, CLA-20 and CM-CLA-20) by the method of Noelting and Bernfeld (1948) using dinitrosalicylic acid (DNS) as a reductimetric agent. 20 mg of each substrate in powder form were swollen and incubated for 3 min at 25° C. in 2 mL of phosphate buffer (0.02 M) containing 18 EU pancreatic α-amylase.

CM-CLA-20 exhibited higher stability to amylolysis than did CLA-20 (FIG. IV). The substrate showing the highest susceptibility to amylase was CLA-6. Without being bound by any particular theory, it appears that a higher degree of cross-linking confers higher stability to amylolysis. Furthermore, the presence of carboxylic (CM) groups seems to limit amylolysis even more. Without being bound by theory, CM groups might block the access of the α-amylase (despite the fact that it is an endo-amylase) to the CM-CLA support by steric hindrance or ionic interactions.

Synthesis of Cross-linked Amylose CLA-35

150 g of amylose was suspended in 375 mL of cold distilled water in a HOBART® mixer (4 L). The suspension was warmed to 50° C. with stirring, and a volume of 500 mL of 1.5 N NaOH (60 g/L) was slowly added (over about 8 min) to the amylose suspension. The medium was maintained for another 20 min at 50° C. with stirring, for gelatinization. Then, 44.2 mL of epichlorohydrin (d=1.19 g/mL) was added slowly (over 5 min), at a constant rate. The reaction medium was maintained under stirring at 50° C. for 1 h to effect cross-linking.

Neutralization was achieved first by adding 570 mL of distilled water to the reaction medium. Then, a solution of acetic acid (85 mL of glacial acetic acid/17.4 M/ in 600 mL distilled water, completed with another volume of 1050 mL distilled water pre-heated at 50° C.) was introduced to the CLA-35 suspension, under stirring, up to a final pH of 6.8–7.0. The suspension was then slowly cooled to 20° C.

A 4 L volume of an acetone/water solution (85/15 v/v) was prepared, and 1 L of this solution was added slowly, under stirring, to a 1 L suspension of CLA-35. This medium was left, under stirring, at 4° C. for 20 min and filtered. The gel remaining on the filter was resuspended in 1 L of acetone/water (60/40 v/v), maintained for 20 min under stirring at 4° C., and filtered. This washing in acetone/water (60/40) was repeated twice.

The gel obtained from the last filtration was recovered and resuspended in 400 mL of acetone. The medium was maintained for 20 min under stirring at 4° C., and filtered. This operation was repeated two more times (but without 20 min at 4° C.) and filtered. The resulting powder was dried by evaporation of acetone.

Synthesis of Carboxymethyl Cross-linked Amylose (CM-CLA-35)

10 g of CLA-35 were suspended in 40 mL of 5 M NaOH. Then, 10 g of monochloroacetic acid (dissolved in 12 mL distilled water) was added to the alkaline suspension of CLA-35. The reaction medium was homogenized for 20 min on an ice bath and then placed in a water bath for 1 h at 75° C., to effect carboxymethylation.

The washing of CM-CLA-35. After the reaction was complete, the suspension was filtered, resuspended in distilled water and filtered again on a Büchner funnel, measuring the pH of filtrate. The gel was thoroughly washed on the filter until the filtrate had a pH of 6.5–7.0. The gel was then resuspended in 1 L of distilled water, and a 1 L solution of acetone/water (85/15 v/v) was added slowly, under stirring, to the suspension. The medium was kept, under stirring, at 4° C. for 20 min, and filtered. The gel remaining on the filter was resuspended in 0.5 L of acetone/water solution (80/20 v/v), maintained for 20 min under stirring at 4° C., and filtered. This washing was repeated once more with acetone/water (90/10).

The gel obtained from the last filtration was recovered, resuspended in 400 mL of acetone, maintained for 20 min under stirring at 4° C., and filtered. This operation was repeated two more times (but without keeping the suspension for 20 min at 4° C.) and filtered. The resulting CM-CLA-35 powder was finally dried by evaporation.

The degree of substitution of hydroxyl groups was evaluated by potentiometric titration of carboxymethyl groups (device: Corning-ion analyser 250) with 0.1 N NaOH calibrated solution. It was of 3.8 meq/g.

Synthesis of Aminoethyl Cross-linked Amylose AE-CLA-35)

Aminoethylation was achieved by treatment of CLA-35 with 2-chloroethylamine hydrochloride.

10 g of CLA-35 were suspended in 40 mL of cold (0–4° C.) 5 M NaOH, homogenized and kept on ice bath for one hour. Then, 12.25 g of chloroethylamine hydrochloride (dissolved in a minimal volume of distilled water) was added to the alkaline suspension of CLA-35, with continuing homogenization for another 20 min on the ice bath. The reaction medium was then placed for 1 h in a water bath at 75° C., effecting aminoethylation. During the reaction, the pH was checked and several mLs of 10 N NaOH were added (in small aliquots) to the gel in order to neutralize the HCl produced during the reaction and to maintain the gel's pH at 9–10.

After the reaction, the suspension was filtered, resuspended in distilled water and filtered again on a Büchner funnel, measuring the pH of filtrate, as for CM-CLA-35 synthesis. The gel was washed on the filter until pH 6.5–7.0, then resuspended in 1 L distilled water. A 1 L solution of acetone/water (85/15 v/v) was added slowly, under stirring, to the suspension. The AE-CLA-35 gel was dried by the same procedures as for CM-CLA-35. The resulting AE-CLA-35 powder obtained was finally dried by evaporation on aluminum sheets.

Susceptibility to Amylolysis of CLA-6, CLA-35, AE-CLA-6, AE-CLA-35 and CM-CLA-35

Figure 5:
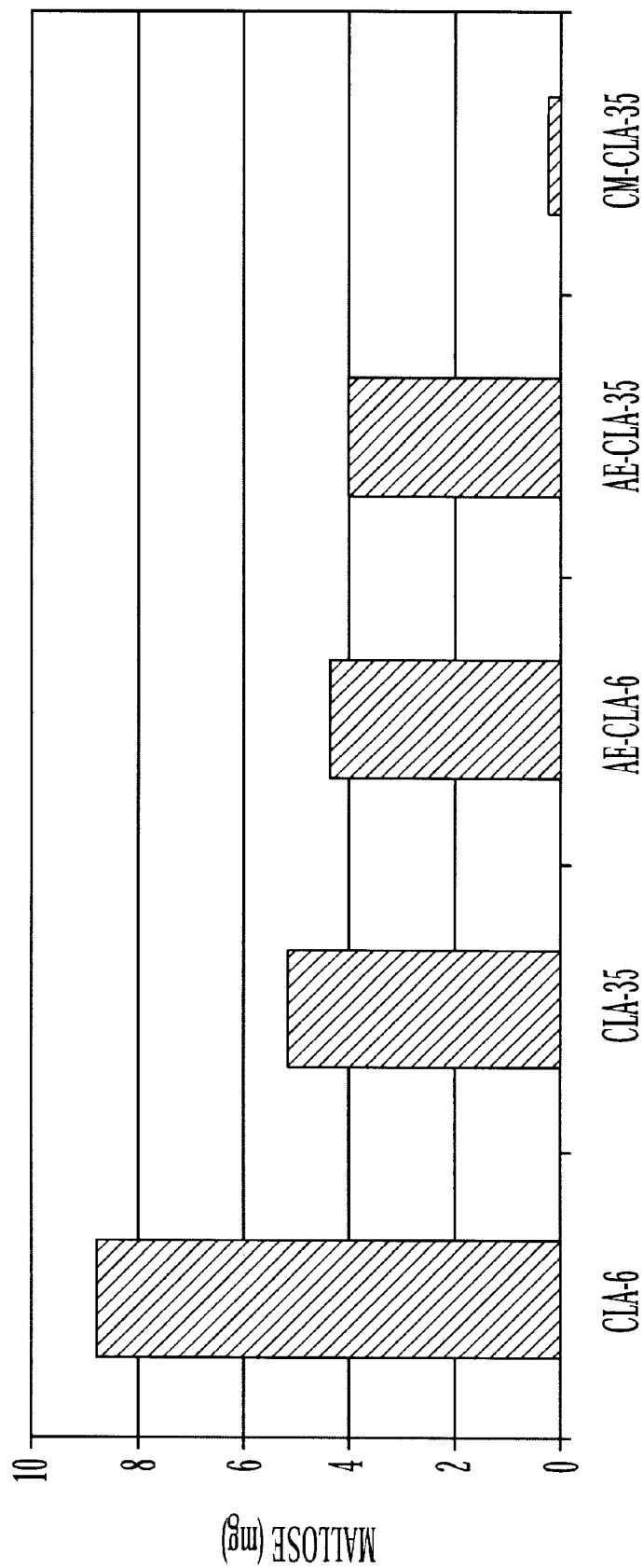
FIG. 5 is a bar graph showing degrees of amylolysis of CLA-6, CLA-35, AE-CLA-6, AE-CLA-35 and CM-CLA-35, as measured by liberation of maltose.

The susceptibility to amylolysis of CLA-6, CLA-35, AE-CLA-6, AE-CLA-35 and CM-CLA-35 were compared. AE-CLA-6 was prepared according to the procedure used to prepare AE-CLA-35, except that CLA-6 was used instead of CLA-35. Amylolysis was quantified from the amounts of maltose liberated during α-amylase attack on the above-mentioned substrates, determined by the method of Noelting and Bernfed (Noelting G. and Bernfed P., Helv. Chim. Acta, 31, 286–293, 1948) with dinitrosalicylic acid (DNS) used as the reductimetric agent. For each derivative, 20 mg of powder was swollen and incubated for 3 min at 25° C. in 2 mL of 0.02 M phosphate buffer containing 18 EU α-amylase. Then, 1 mL of 1% DNS was added (stopping the enzymatic reaction), and the mixture was incubated in a boiling water bath for 5 min to allow liberated reducing sugars to react with DNS. The samples were then placed in a water bath at 0° C., and diluted with 15 mL of distilled water, prior to reading absorbances at 535 nm. As shown in Figure 5, aminoethylation or carboxymethylation of amylose substrates reduced the degree of amylolysis (as measured by amounts of liberated maltose). In fact, the susceptibility to amylolysis of AE-CLA-6 was reduced to 50% relative to that of CLA-6. Moreover, CM-CLA-35 was virtually immune from amylolytic degradation by α-mylase.

Drug Release in vitro

Example 1

10% Acetaminophen Tablets

| |
|---|
| CLA (x = 3.25) 90% |
| Acetaminophen 10% |

Method

The CLA used in this example was with sodium trimetaphosphate. The drug was mixed with CLA in a bag for 2–3 minutes and the blend was compressed using a tablet press with round 5/16 inch toolings. The weight of the tablets was 200 mg.

Example 2

10% pseudoephedrine tablets

| |
|---|
| CLA (x = 3.25) 90% |
| Pseudoephedrine HCl 10% |

Method

The CLA used in this example was with sodium trimetaphosphate. The drug was mixed with CLA in a bag for 2–3 minutes and the blend was compressed using a tablet press with round 15/32 inch toolings. The weight of the tablets was 500 mg.

Test Procedure

The dissolution release profile of the tablets was determined using a USP type III dissolution apparatus. The dissolution system was set up with different dissolution fluids that mimic the GI tract environment with or without α-amylase(4500 I.U./L). One international unit (I.U.) will liberate 1 mg of maltose from starch in three minutes at pH 6.9 at 20° C. The drug release was recorded spectrophotometrically with an automated sampling system.

Example 3

20% Acetaminophem Tablets

| |
|---|
| CLA (or derivatives) 80% |
| Acetaminophen 20% |

Method 500 mg tablets having a 13 mm diameter and a 2.4–2.7 mm thickness were prepared by direct compression in a hydraulic Carver press at 3 T/cm², and contained 100 mg acetaminophen as tracer. The acetaminophen tracer and the CLA (or derivatives) powders were mixed for three minutes prior to compression.

Test Procedure

Tablets were placed individually in 1 L buffered solutions (0.05 M phosphate buffer, pH 7, at 37° C. in a USP dissolution apparatus (rotating paddle at 50 rpm), and the acetaminophen release data recorded (HP spectrophotometer with a dissolution software). The release of acetaminophen was measured spectrophotometrically ($\lambda$=280 nm), using a closed circulating system.

Results

Figure 6:
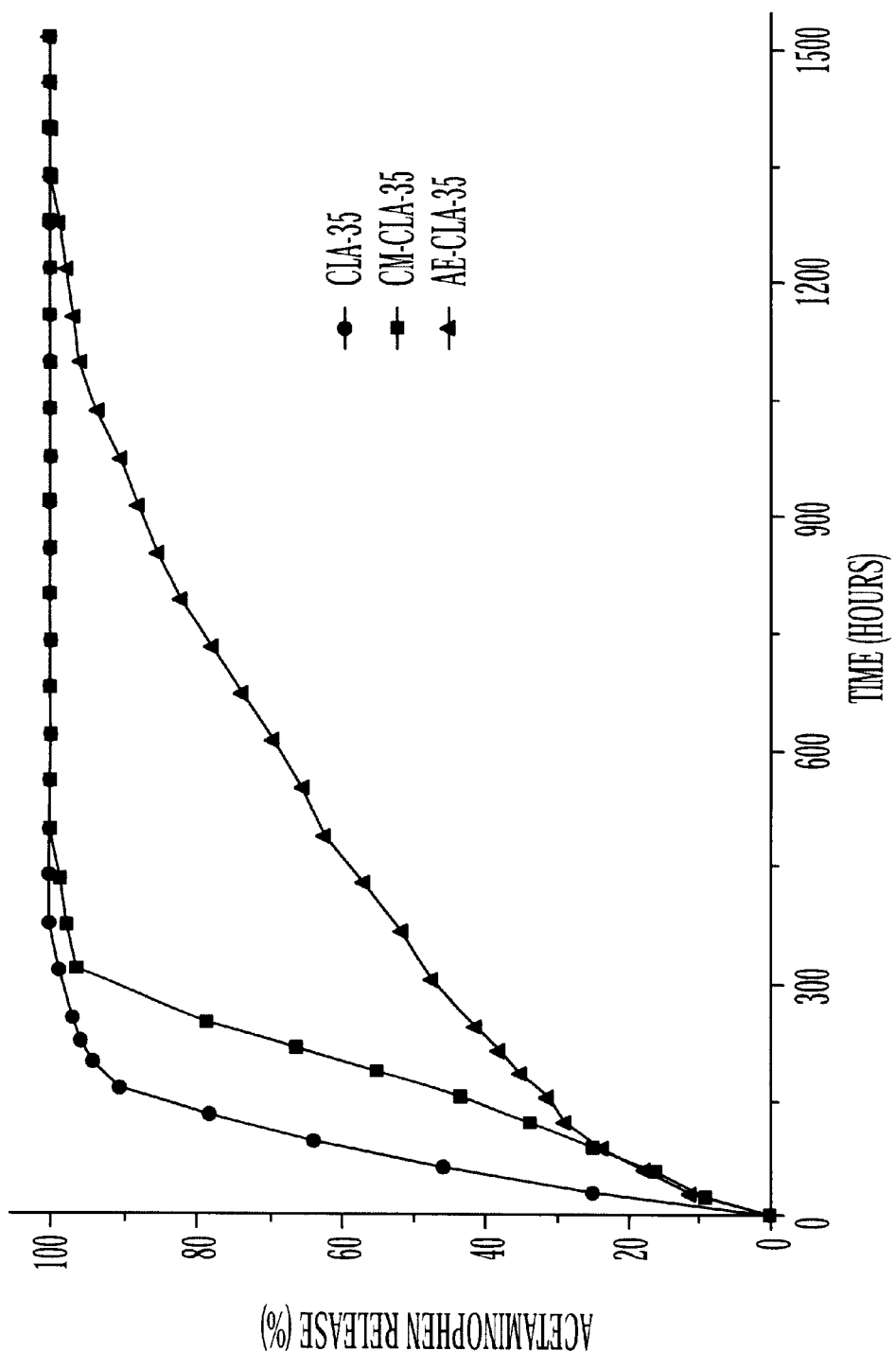
FIG. 6 is a line graph showing kinetic profiles of acetaminophen release from tablets containing CLA-35, CM-CLA-35 or AE-CLA-35 matrices.
Figure 7:
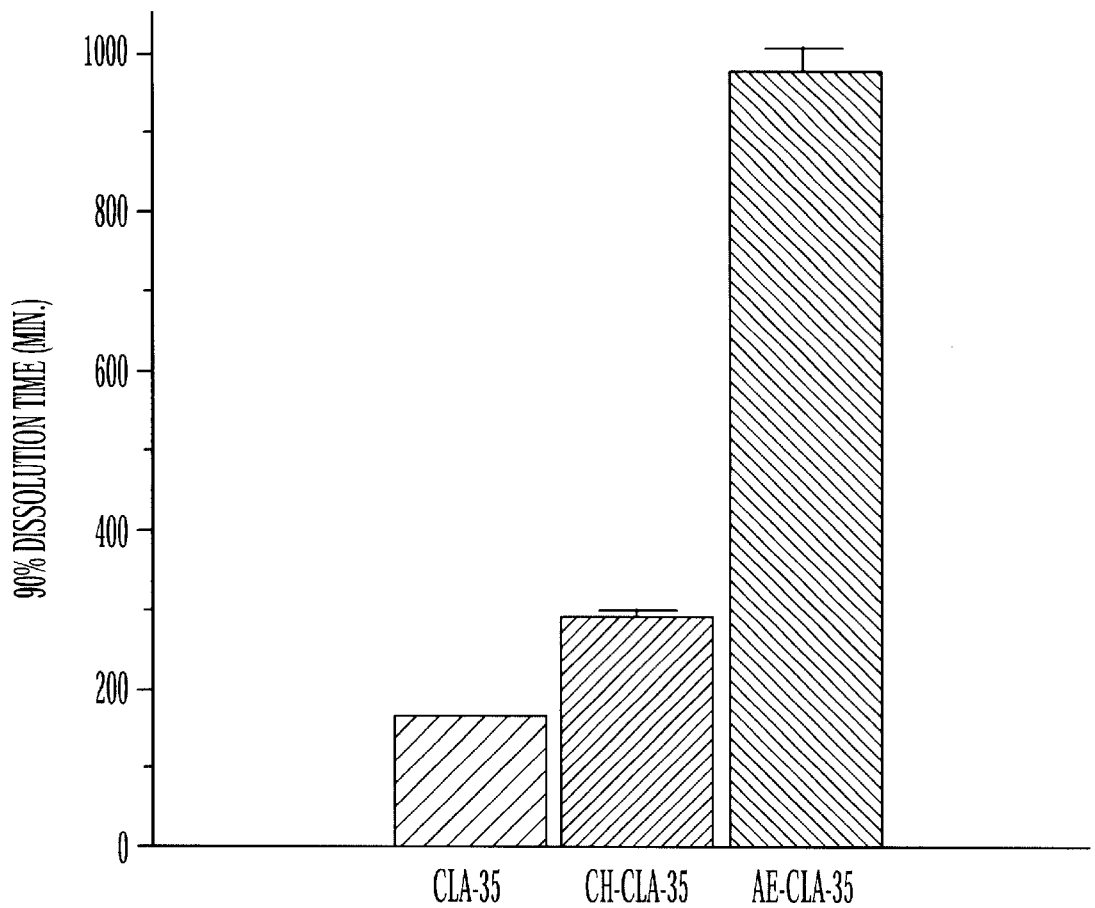
FIG. 7 is a bar graph showing times for release of 90% acetaminophen from tablets containing CLA-35, CM-CLA-35 or AE-CLA-35 matrices.

The kinetic profiles of the acetaminophen release from tablets containing CLA-35, CM-CLA-35 or AE-CLA-35 matrices are presented in FIG. 6. Both CM-CLA-35 and AE-CLA-35 derivatives provide longer release times than does CLA-35.

Carboxymethylation of amylose results in an increase of about 2–3 hrs in the dissolution time; from 2–3 h for CLA-35 (90% release), to 4–6 h for CM-CLA-35 (90% release). A substantial increase in dissolution time (up to 16–17 h for 90% release), was found for AE-CLA-35 (22–24 h for the total release).

In Vitro Dissolution of Tablets Containing Aminoethyl Amylose and Diclofenac Sodium 200 mg round, flat tablets being 8.73 mm in diameter and 2.51–2.74 mm in thickness, and containing 10 mg of diclofenac sodium and 190 mg of AE-CLA-35, were compressed using a single punch Stokes F4 tablet press (tooling: 8.73 mm round flat punches; upper compression force: 4–50 kN). The tablets were subjected to in vitro dissolution using a USP type III apparatus at 10 dips/min and 37% in USP phosphate buffer (pH=6.8) with or without amylase enzyme at 9000 IU/L (n=3). Experiments performed in the presence of enzyme approximate physiological conditions. Release of diclofenac sodium was quantified using UV detection at 276 nm.

Figure 8:
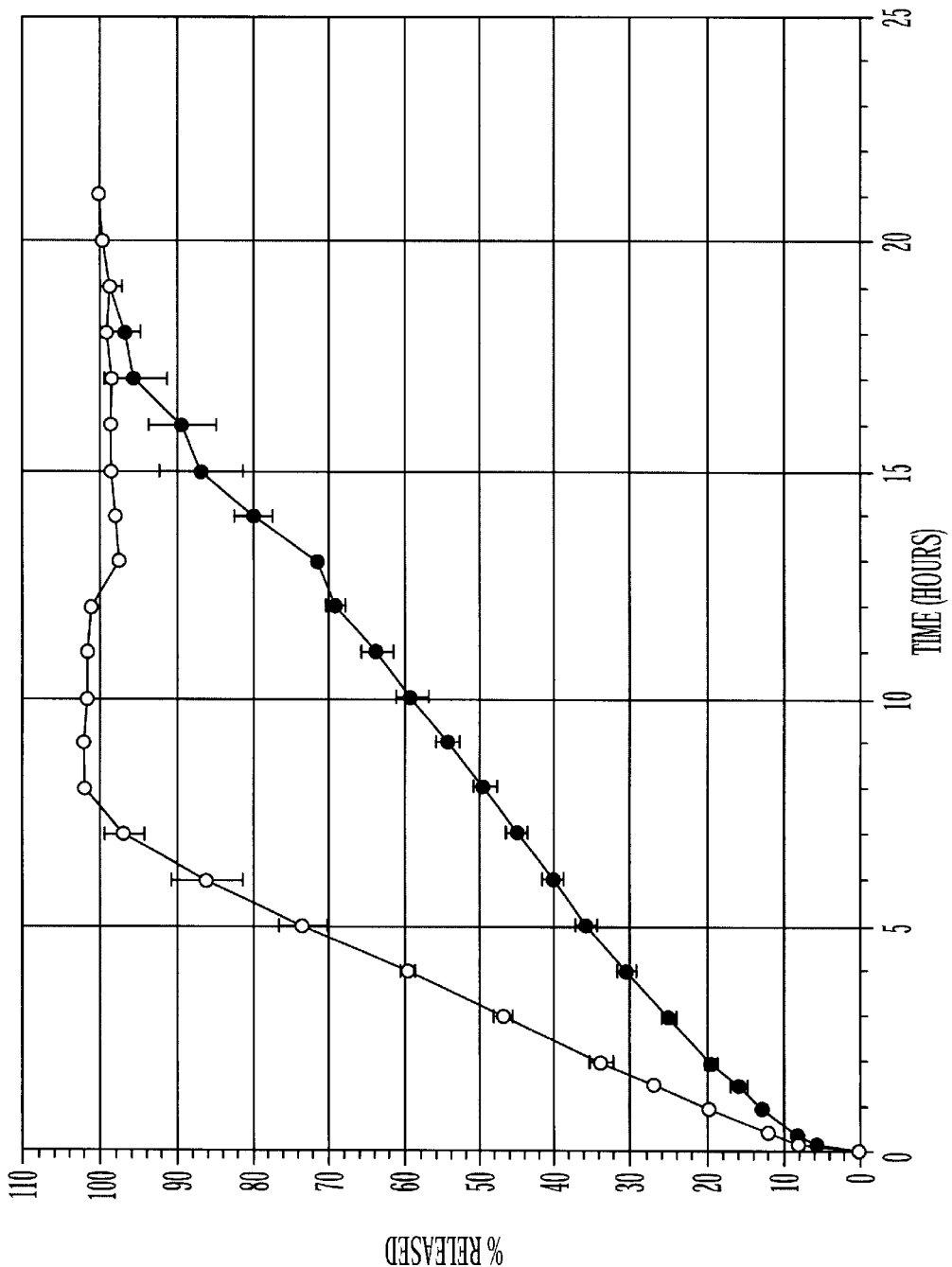
FIG. 8 is a line graph showing percent release of diclofenac sodium from tablets, containing aminoethyl cross-linked amylose, that were dipped in USP phosphate buffer (pH=6.8). The symbol "-●-" is used to depict data for phosphate buffer without amylase enzyme; the symbol "-○-" is used to depict data for phosphate buffer with amylase enzyme (9000 IU/L).

As shown in FIG. 8, 100% of the diclofenac sodium was released after 8 min of dipping in phosphate buffer that contained enzyme. However, 100% of the diclofenac sodium is released in a shorter time under similar conditions when amylose that is not modified with groups having functional groups is used as a carrier polymer.

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

We claim:

1. Cross-linked high amylose starch having functional groups, prepared by a process comprising the steps of:
   (a) reacting high amylose starch with a cross-linking agent cross-linked a concentration of about 0.1 g to about 40 g of cross-linking agent per 100 g of high amylose starch to afford cross-linked amylose; and
   (b) reacting the cross-linked high amylose starch with a functional group-attaching reagent at a concentration of about 75 g to about 250 g of functional group-attaching reagent per 100 g of cross-linked amylose to afford the cross-linked amylose having functional groups, wherein the functional group attaching reagent is selected from the group consisting of monochloroacetic acid and chloroethylamine hydrochloride.

2. The cross-linked amylose of claim 1, wherein the cross-linking agent is selected from the group consisting of 2,3-dibromopropanol, epichlorohydrin, sodium trimetaphosphate, linear mixed anhydrides of acetic and di- or tribasic carboxylic acids, vinyl sulfone, diepoxides, cyanuric chloride, hexahydro-1,3,5-trisacryloyl-s-triazine, hexamethylene diisocyanate, toluene 2,4-diisocyanate, N,N-methylenebisacrylamide, N,N'-bis (hydroxymethyl) ethyleneurea, phosgene, tripolyphosphate, mixed carbonic-carboxylic acid anhydrides, imidazolides of carbonic and polybasic carboxylic acids, imidazolium salts of polybasic carboxylic acids, guanidine derivatives of polycarboxylic acids, and esters of propanoic acid.

3. The cross-linked high amylose starch of claim 2, wherein the cross-linking agent is epichlorohydrin.

4. The cross-linked high amylose starch of claim 1, wherein the reacting of step (a) is carried out at a concentration of about 35 g of epichlorohydrin per 100 g of high amylose starch.

5. The cross-linked high amylose starch of claim 1, wherein the reacting of step (b) is carried out at a concentration of about 100 g of monochloracetic acid per 100 g of high amylose starch.

6. The cross-linked high amylose starch of claim 1, wherein the reacting of step (b) is carried out at a concentration of about 122.5 g of 2-chloroethylamine hydrochloride per 100 g of high amylose starch.

* * * * *